US00PP23541P2

(12) United States Plant Patent
Smith

(10) Patent No.: US PP23,541 P2
(45) Date of Patent: Apr. 16, 2013

(54) *CHRYSANTHEMUM* PLANT NAMED 'SYMARJ COL'

(50) Latin Name: *Chrysanthemum×morifolium*
Varietal Denomination: Symarj Col

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 255 days.

(21) Appl. No.: 13/065,921

(22) Filed: Apr. 1, 2011

(51) Int. Cl.
*A01H 5/00* (2006.01)

(52) U.S. Cl. ..... Plt./293; Plt./287

(58) Field of Classification Search ..... Plt./287, Plt./293
See application file for complete search history.

*Primary Examiner* — Susan McCormick Ewoldt
(74) *Attorney, Agent, or Firm* — Joshua L. Price

(57) ABSTRACT

A new *Chrysanthemum* plant named 'Symarj Col' particularly distinguished by the long-lasting coral-red inflorescences, medium green foliage, rounded and mounded plant habit, and a natural flowering season of about early October.

1 Drawing Sheet

Latin name of the genus and species of the plant claimed: *Chrysanthemum×morifolium.*

Varietal denomination: 'Symarj Col'.

BACKGROUND OF THE NEW PLANT

The present invention comprises a new *Chrysanthemum*, botanically known as *Chrysanthemum×morifolium*, and hereinafter referred to by the variety name 'Symarj Col'.

'Symarj Col' is a product of a planned breeding program. The new cultivar has long lasting coral-red inflorescences, medium green foliage, rounded and mounded plant habit, and a natural flowering season of about early October.

'Symarj Col' originated from a hybridization made in October 2005 in a controlled breeding environment in Tenjo, Columbia. The female parent was the proprietary plant designated '03-M341', unpatented, with lavender inflorescences, smaller plant size and a natural season flowering response that is two weeks faster.

The male parent of 'Symarj Col' was an proprietary plant designated as '00-M401' with a similar inflorescence color, more disc florets, a color that doesn't last as long, and a natural season flowering response that is two weeks faster. The resultant seed was sown in June 2006 in Alva Fla.

'Symarj Col' was selected as one flowering plant within the progeny of the stated cross in the November 2006 in a controlled environment in Alva, Fla.

The first act of asexual reproduction of 'Symarj Col' was accomplished when vegetative cuttings were propagated from the initial selection in January 2007 in a controlled environment in Alva, Fla.

BRIEF SUMMARY OF INVENTION

Horticultural examination of plants grown from cuttings of the plant initiated in January 2007, and continuing thereafter, has demonstrated that the combination of characteristics as herein disclosed for 'Symarj Col' are firmly fixed and are retained through successive generations of asexual reproduction.

'Symarj Col' has not been observed under all possible environmental conditions. The phenotype may vary significantly with variations in environment such as temperature, light intensity and day length.

A Plant Breeder's Right for this cultivar was applied for in Canada on Apr. 9, 2010 (No. 10-6932). 'Symarj Col' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Symarj Col' with colors being as true as possible with an illustration of this type. The photographic drawing shows a flowering potted plant of the new variety.

DETAILED BOTANICAL DESCRIPTION

The plant used for the photographs was about 16 weeks old grown in Monroeville, N.J. in an outdoor trial. One rooted cuttings grown in a nine inch pot with no terminal pinching of the apices. The photograph was taken in mid October 2010 in New Jersey.

The plant descriptions and measurements were taken in Gilroy, Calif. in early October 2010 under natural light. Plants were grown in an 8 inch pot with only one plant and grown in a greenhouse. These plants used in the descriptions were about 16 weeks old.

Color references are made to The Royal Horticultural Society Colour Chart (R.H.S.) 2001.

TABLE 1

DIFFERENCES BETWEEN THE NEW VARIETY 'SYMARJ COL' AND A SIMILAR VARIETY

| | 'Symarj Col' | 'Flamingo' (Unpatented) |
|---|---|---|
| Flowering uniformity: | More uniformity/less tiering | Less uniformity/more tiering |
| Natural season flowering response: | 1 week slower | 1 week faster |
| Shaded flowering response: | 10 days faster | 10 days slower |

Plant:

*Form, growth and habit*.—Herbaceous decorative garden-type, stems upright and outwardly spreading, freely branching, strong and moderately vigorous growth habit.

*Plant height*.—25 cm.

*Plant height* (*inflorescence included*).—33-35 cm.

*Plant width*.—70 cm.

*Garden performance and tolerance to weather*.—Very good.

Roots:

*Number of days to initiate roots*.—4 days at about 22 degrees C.

*Number of days to produce a rooted cutting*.—10-12 days at 22 degrees C.

*Type*.—Fine, fibrous, free branching.

*Color*.—RHS N155B but whiter.

Foliage:

*Arrangement*.—Alternate.

*Immature, leaf color, upper surface*.—RHS 137A.

*Lower surface*.—Between RHS 137C and RHS 137D.

*Mature, leaf color, upper surface*.—RHS 137A.

*Lower surface*.—Between RHS 137C and RHS 137D.

*Length*.—3.0-3.5 cm.

*Width*.—2.0-2.3 cm.

*Shape*.—Broadly ovate.

*Base shape*.—Attenuate.

*Apex shape*.—Mucronulate.

*Margin*.—Irregularly and palmately lobed; serrate.

*Texture, upper surface*.—Bifid T-shaped hairs.

*Lower surface*.—Bifid T-shaped hairs.

*Color of veins, upper surface*.—RHS 147C.

*Color of veins, lower surface*.—RHS 147C.

*Petiole color*.—RHS 147C.

*Length*.—0.6-0.7 cm.

*Diameter*.—0.2 cm.

*Texture*.—Bifid T-shaped hairs.

Stem:

*Quantity of main branches per plant*.—10 plus many secondary.

*Color of stem*.—RHS 147C.

*Length of stem*.—20-23 cm.

*Diameter*.—0.35-0.5 cm.

*Length of internodes*.—1.5-2.0 cm.

*Texture*.—Bifid T-shaped hairs.

*Color of peduncle*.—RHS 147C.

*Length of peduncle*.—4.5-5.0 cm.

*Peduncle diameter*.—0.15 cm.

*Texture*.—Bifid T-shaped hairs.

Inflorescence:

*Type*.—Compositae type, solitary inflorescences decorative-type, borne terminally above foliage, ray florets arranged acropetally on a capitulum.

*Quantity of short days to flowering* (*response time*).—About 49 days.

*Quantity of inflorescences per plant*.—Approximately 300.

*Lastingness of individual blooms on the plant*.—About 6 weeks from the first color.

*Fragrance*.—Slightly spicy.

Bud (just when opening/showing color):

*Color*.—RHS 51C with RHS 51B apex.

*Length*.—0.7-0.8 cm.

*Width*.—0.8-1.0 cm.

*Shape*.—Oblate.

Immature inflorescence:

*Diameter*.—1.75-2.0 cm.

*Color of ray florets, upper surface*.—A slight RHS 1C basally, with RHS 39A overlay.

*Lower surface*.—RHS 39B to 39C and RHS 51B to RHS 51C at tip.

Mature inflorescence:

*Diameter*.—2.5-2.8 cm.

*Depth*.—1.2-1.4 cm.

*Total diameter of 'disc'*.—N/A.

*Receptacle height*.—0.2-0.3 cm.

*Receptacle diameter*.—0.3-0.4 cm.

Ray florets:

*Average quantity of florets*.—Approximately 300 in numerous whorls.

*Color of florets, upper surface*.—A slight RHS 1C basally, with RHS 39A over lay, fading to more RHS 39B.

*Lower surface*.—RHS 39C and RHS 51C at apex.

*Length*.—1.0 cm.

*Width*.—0.3-0.4 cm.

*Shape*.—Elliptical.

*Apex shape*.—Praemorse.

*Margin*.—Entire.

*Texture, upper surface*.—Papillose.

*Lower surface*.—Papillose.

Disc florets:

*Average quantity of florets*.—None observed.

*Color of florets*.—N/A.

*Length*.—N/A.

*Width*.—N/A.

*Shape*.—N/A.

*Apex shape*.—N/A.

Phyllaries:

*Quantity*.—25-30.

*Color, upper surface*.—RHS 147B.

*Lower surface*.—RHS 147B.

*Length*.—0.3-0.4 cm.

*Width*.—0.1-0.15 cm.

*Shape*.—Lanceolate.

*Apex shape*.—Acute.

*Based*.—Fused.

*Margins*.—Entire.

*Texture, upper surface*.—Glabrous.

*Lower surface*.—Bifid T-shaped hairs.

Reproductive organs:

*Pistil*.—None observed.

*Length*.—N/A.

*Style color*.—N/A.

*Style length*.—N/A.

*Stigma color*.—N/A.

*Stigma shape*.—N/A.

*Ovary color*.—N/A.

*Stamens*.—None observed.
*Color of filaments*.—N/A.
*Length filaments*.—N/A.
*Anther color*.—N/A.
*Anther length*.—N/A.
*Anther shape*.—N/A.
*Color of pollen*.—N/A.
*Pollen amount*.—N/A.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Symarj Col' substantially as illustrated and described herein.

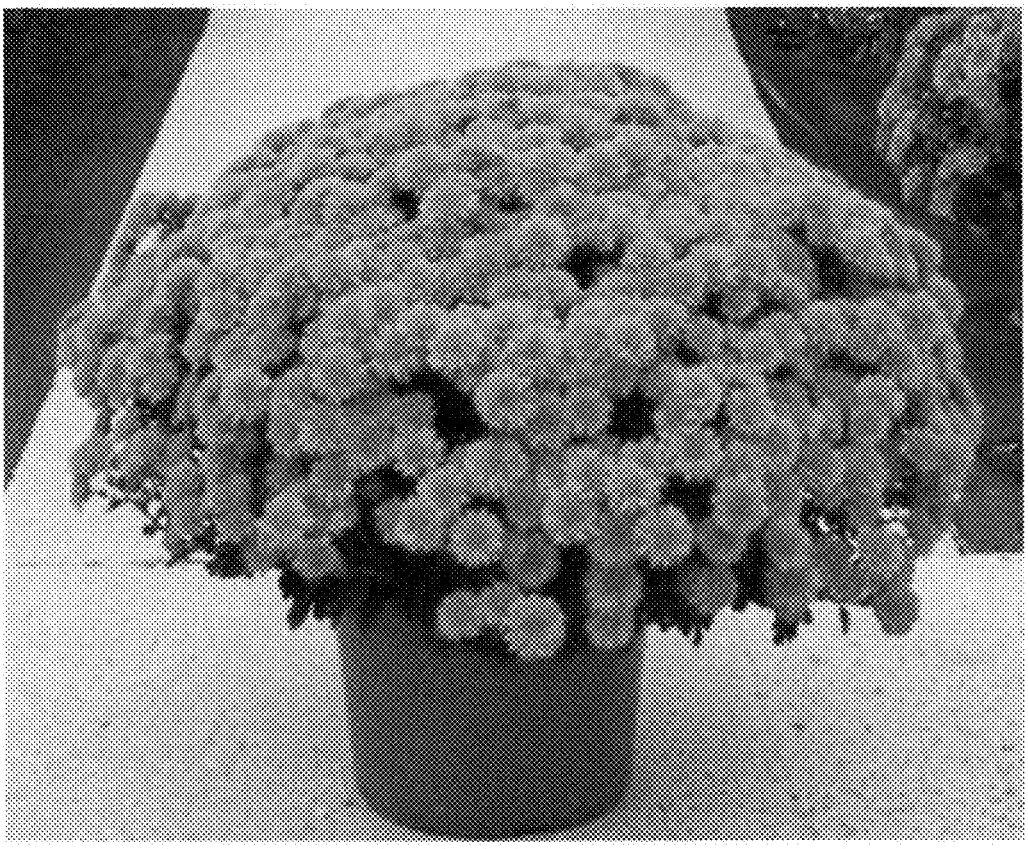

* * * * *